US00PP19529P2

(12) United States Plant Patent
Bradford

(10) Patent No.: US PP19,529 P2
(45) Date of Patent: Dec. 2, 2008

(54) INTERSPECIFIC TREE NAMED 'APRIPLUM VII'

(50) Latin Name: ***Prunus* sp.**
Varietal Denomination: Apriplum VII

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,894

(22) Filed: Nov. 26, 2007

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP14,196 P2 9/2003 Bradford
PP16,461 P2 4/2006 Bradford

*Primary Examiner*—S. B. McCormick-Ewoldt

(57) ABSTRACT

The present invention relates to an interspecific tree and more particularly to a new and distinct variety broadly characterized by a medium size, vigorous, hardy, and productive tree. The variety is self-unfruitful, blooms during the mid season, and requires cross pollination. The fruit matures under the ecological conditions described during mid August, with first picking on Aug. 18, 2007. The fruit is uniformly small to medium in size, nearly black in skin color, clingstone in type, heart shaped, red and orange in flesh color, firm in texture, and outstanding in flavor with a strong apricot presence.

1 Drawing Sheet

Botanical classification: *Prunus* sp.
Varietal denomination: 'Apriplum VII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Apriplum VII'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2000 one such house containing an unpatented interspecific tree that produced fruit with purple skin and orange flesh, code named 7P1017, was crossed by me in this manner. To pollinate this tree, I selected bouquets from several sources of apricot, plum, and interspecific plum-apricot hybrid trees without keeping specific written details. Upon reaching maturity the fruit from this tree was harvested and the seeds were removed, cracked, stratified and germinated as a group with the label "H19 7P1017". They were grown as seedlings on their own root in my greenhouse and upon reaching dormancy transplanted to a cultivated area of my experimental orchard lcoated near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'Plumsweettwo' (U.S. Plant Pat. No. 14,196) plum by being self-unfruitful and by producing fruit that is clingstone in type, nearly black in skin color, red to orange in flesh color, and is excellent in flavor, but is distinguished therefrom by producing fruit that is somewhat smaller in size, that is heart shaped instead of globose, that has a less distinguishable suture, that has less pronounced skin freckling, that matures about twenty-five days later, and that has a strong presence of apricot in flavor.

SUMMARY OF VARIETY

The present interspecific variety is characterized by a medium size, vigorous, hardy, and productive tree. Being self-unfruitful, the present variety requires cross pollination from an mid seasonal to late blooming apricot, interspecific, or plum, such as 'Plumsweet IV' (U.S. Plant Pat. No. 16,461). The present variety's abundance of blossoms and moderate pollen production entices strong bee activity to facilitate pollination. The fruit matures under the ecological conditions described during mid August, with first picking on Aug. 18, 2007. The fruit is uniformly small to medium in size, nearly black in skin color, clingstone in type, heart shaped, red and orange in flesh color, firm in texture, and outstanding in flavor with a strong apricot presence.

DRAWING

The accompanying photograph consists of four whole fruits positioned to display the characteristics of the skin color and form, two half fruits divided to reveal the flesh and stone, typical leaves, and three insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full ripe on Aug. 26, 2007, on the original tree during its sixth growing season. The flower and bud descriptions were developed during the previous blooming season. All major color code designations are by reference to the Inter-Society Color Council, National Bureau of Standards. Common color names are also used occasionally.

Parentage

Seed parent: '7P1070' interspecific (unpatented).
Pollen parent: Unknown.

Tree

Size: Medium, reaching and maintaining a height of 11' [3.35 m.] and a spread of 6' [1.83 m.] after seven growing seasons utilizing typical dormant pruning.

Vigor: Vigorous, responding typically to irrigation and fertilization. The variety grows about 4 ' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable late seasonal blooming apricot, plum or interspecific, such as 'Plumsweet IV' (U.S. Plant Pat. No. 16,461) interspecific tree.

Bearing: Regular bearer, with no crop failures observed.

Trunk:

- *Size*.—Large, reaching a maximum diameter of 5" [127 mm.] after the seventh growing season.
- *Texture*.—Shaggy.
- *Bark color*.—A Dark grayish brown [62. d.gy.Br] and Deep yellowish brown [75. deep yBr] variegation with Moderate orange yellow [71. m.OY] crevices present.
- *Lenticels*.—Approximate Number Per Square Inch: 5. Color: Deep orange yellow [69. deep OY]. Average Size: ¼" [6.4 mm.]. Shape: Eye-shaped to elongated.

Branches:

- *Size*.—Diameter of limb is 2" [51 mm.] measured 12" above the crotch, 1" [25 mm.] measured 12" above the first fork.
- *Texture*.—Smooth on first and second year wood, increasing roughness with age.
- *Color*.—1st Year Wood Topside: Strong brown [55. s.Br]. 1st Year Wood Underside: Brilliant yellow green [116. brill.YG]. Older Wood: Grayish brown [61. gy.Br].
- *Lenticels*.—Number Per Square Inch: More than 60 on second year wood. Color: Brilliant orange yellow [67. brill.OY]. Average size: 1/64" [0.4 mm.]. Shape: Elongated, rectangular.

Leaves:

- *Size*.—Large. Average Length: 4" [102 mm.]. Average width: 1⅝" [41 mm.].
- *Arrangement*.—Alternate.
- *Thickness*.—Medium.
- *Form*.—Elliptical.
- *Apex*.—Acute to Acuminate.
- *Base*.—Acute with an average angle base angle of 80 degrees.
- *Surface*.—Smooth.
- *Color*.—Dorsal Surface: Moderate olive green [125. m.OIG]. Ventral Surface: Moderate yellow green [120. m.YG].
- *Margin*.—Finely serrate.
- *Venation*.—Pinnately net veined.
- *Petiole*.—Average Length: ½" [12.7 mm.]. Average Thickness: 1/16" [1.6 mm.]. Color: Light yellow green [119. l.YG] with a Moderate yellowish pink [29. m.yPk] tinge where exposed to direct sunlight.
- *Stipules*.—Number: 2 per leaf, up to 6 per growing tip. Average Length: 7/16" [11.1 mm.]. Color: Moderate yellow green [120. m.YG] becoming Dark reddish brown [44. d.rBr] with age.
- *Glands*.—Number: Mostly 2 per leaf. Position: Alternately positioned at the intersection of the petiole and the leaf blade. Size: Small. Form: Globose. Color: Light yellow green [119. l.YG] becoming Grayish reddish grown [46. gy.rBr] in the center with age.
- *Leaf buds*.—Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, typically thirty or more stamens, five sepals and petal locations alternately positioned.

- *Average flower diameter*.—1 1/16" [27.0 mm.].
- *Number of petals*.—Five, no double blossoms observed.
- *Petal shape*.—Oval to circular.
- *Petal margin*. —Entire, smooth, wavy.
- *Average petal diameter*.—½" [12.7 mm.].
- *Average petal length*.—9/16" [14.3 mm.].
- *Petal apex*.—Rounded.
- *Petal base*.—Obtuse.
- *Petal color*.—White [263. White] on both sides.
- *Anther color*.—Brilliant yellow [83. brill.Y].
- *Stigma color*.—Light greenish yellow [101. l.gY].
- *Sepal color*.—Very yellow green [115. v.YG].
- *Sepal length*.—5/32" [4.0 mm.].
- *Sepal width*.—5/32" [4.0 mm.].
- *Sepal apex*.—Rounded to elliptical to match the width and length.
- *Sepal margin*.—Fairly smooth to the naked eye, slightly serrate when magnified.

*Average pistil length*.—⅝" [15.9 mm.].
*Average stamen length*.—½" [12.7 mm.].
*Fragrance*.—Moderate.
*Pollen production*.—Moderate.
*Blooming period*.—Medium, three days after 'Santa Rosa' plum (unpatented).
*Onset of bloom*.—One percent on Mar. 3, 2007.
*Date of full bloom*.—Mar. 9, 2007.
*Duration of bloom*.—One to two weeks, dependent on ambient temperature.
*Bloom density*.—Heavy.
*Number per cluster*.—2 to 9, average 4.

FRUIT

Maturity when described: Full ripe, Aug. 26, 2007.
Date of first picking: Aug. 18, 2007.
Date of last picking: Aug. 28, 2007.
Size: Uniform, Small to medium.
*Average diameter axially*.—2⅜" [60.3 mm.].
*Average diameter across cheek plane*.—2⅛" [54.0 mm.].
*Average diameter across suture plane*.—2⅛" [54.0 mm.].
*Typical weight*.—3.2 ounces [91 grams].
Form: Variable, heart shaped, asymmetrical.
*Longitudinal secton form*.—Cordate.
*Transverse section through diameter*.—Round.
Suture: A very inconspicuous line extending from the base to the apex.
Ventral surface: Rounded, slightly lipped toward the base.
Lips: Equal.
Cavity: Rounded, flaring, suture showing on one side.
*Depth*.—¼" [6.4 mm.].
*Breadth*.—9/16" [14.3 mm.].
Base: Truncate, slightly cordate if viewed parallel to the suture.
Apex: Cuneate, protruding.
Pistil point: An inconspicuous dot.
Stem: Medium.
*Average length*.—⅜" [9.5 mm.].
*Average width*.—5/64" [2.0 mm.].
Skin:
*Thickness*.—Medium.
*Surface*.—Smooth.
*Tenacity*.—Tenacious to the flesh.
*Astringency*.—Moderate.
*Tendency to crack*.—Slight.
*Color*.—Blackish red [21. blackish R] with very small Light grayish red [18. l gy.R] freckling throughout.
*Bloom*.—Abundant.
Flesh:
*Color*.—Deep red [13. deep R] toward the skin, Strong reddish orange [35. s.rO] toward the stone.
*Surface of pit cavity*.—Covered with Strong red [12. s.R] broken fibers when twisted from the stone.
*Amygdalin*.—Moderate.
*Juice*.—Moderate, rich.
*Texture*.—Firm, crisp.
*Fibers*.—Abundant, fine, tender.
*Ripens*.—Slightly earlier toward the apex.
*Flavor*.—A tasty blend of acid and sugar with strong apricot flavor, typically 20 to 24 brix.
*Aroma*.—Moderate.
*Eating quality*.—Outstanding.

STONE

Type: Clingstone.
Form: Oval.
Hilum: Narrow.
Base: Rounded.
Apex: Acuminate, with a sharp 1/16" [1.6 mm.] tip.
Sides: Equal.
Surface: Rough throughout with a groove from base to apex on each side of the dorsal fin.
External color of stone: Brownish orange [54. brO].
Pit wall color when cracked: Strong yellowish brown [74. s.yBr].
Cavity surface color: Light olive brown [94. l.OlBr].
Average pit wall thickness: 1/16" [1.6 mm.].
Average width: ⅝" [15.9 mm.].
Average length: 1" [25.4 mm.].
Average breadth: 7/16" [11.1 mm.].
Tendency to split: None observed.
Kernel:
*Form*.—Oval.
*Skin color*.—Light yellow [86. l.Y] when first removed.
*Pellicle color*.—Dark olive [108. d.Ol].
*Vein color*.—Light olive [106. l.Ol].
*Taste*.—Bitter.
*Viable*.—Yes.
*Average width*.—7/16" [11.1 mm.].
*Average length*.—9/16" [14.3 mm.].
*Amygdalin*.—Moderate.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditons at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunun* sp. tree, substantially as illustrated and described, that is similar to 'Plumsweettwo' (U.S. Plant Pat. No. 14,196) plum by being self-unfruitful and by producing fruit that is clingstone in type, nearly black in skin color, red to orange in flesh color, and is excellent in flavor, but is distinguished therefrom by producing fruit that is somewhat smaller in size, that is heart shaped instead of globose, that has a less distinguishable suture, that has less pronounced skin freckling, that matures about twenty-five days later, and that has a strong presence of apricot in flavor.

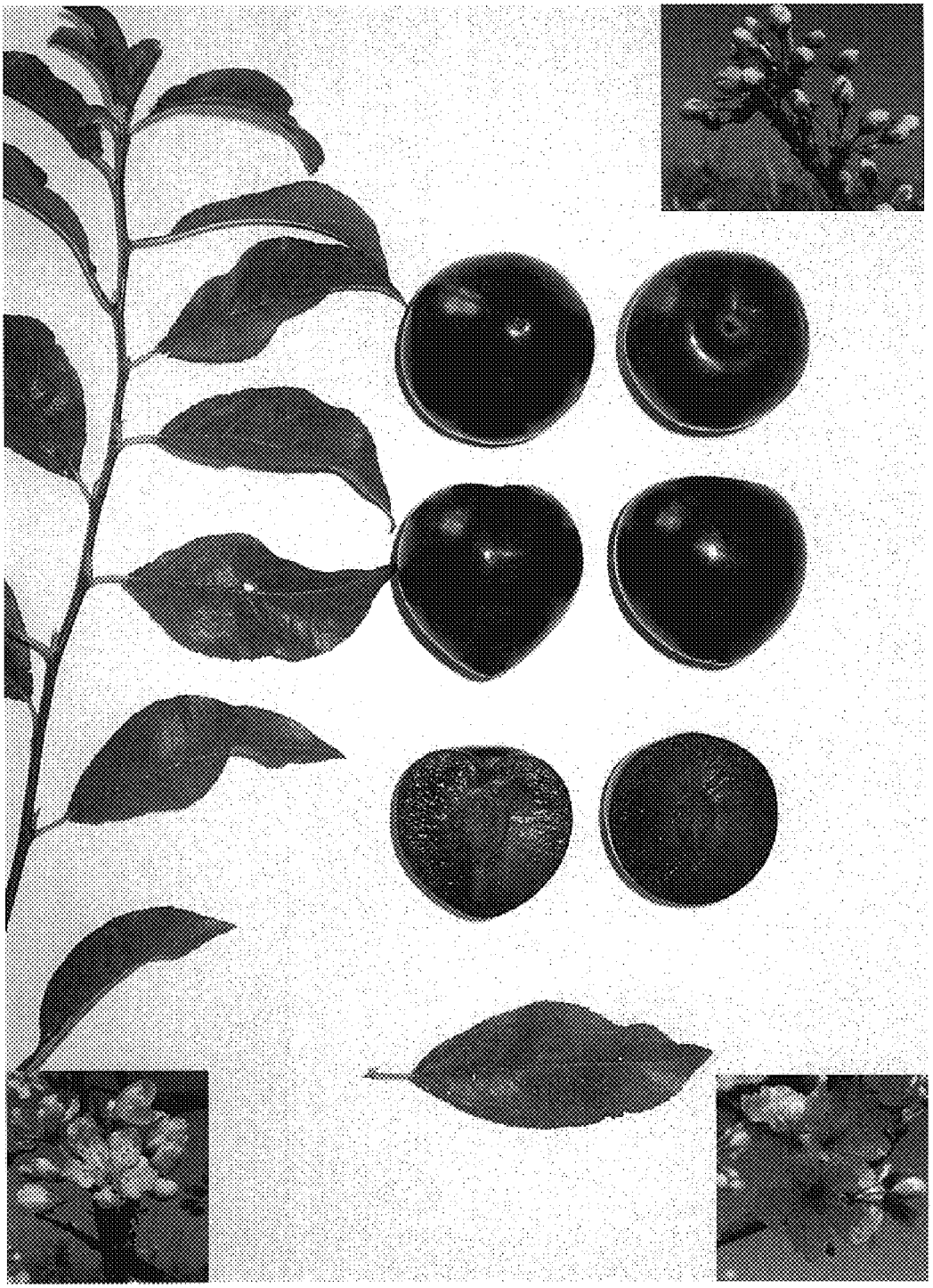

* * * * *